United States Patent
Edwards

(10) Patent No.: US 6,953,766 B2
(45) Date of Patent: Oct. 11, 2005

(54) PREPARATION OF EFFICIENT REPO AND LAPO CATALYSTS

(75) Inventor: Charles Lee Edwards, Houston, TX (US)

(73) Assignee: Shell Oil Company, Houston, TX (US)

( * ) Notice: Subject to any disclaimer, the term of this patent is extended or adjusted under 35 U.S.C. 154(b) by 168 days.

(21) Appl. No.: 10/382,544

(22) Filed: Mar. 6, 2003

(65) Prior Publication Data

US 2004/0039076 A1 Feb. 26, 2004

Related U.S. Application Data

(60) Provisional application No. 60/405,552, filed on Aug. 23, 2002.

(51) Int. Cl.[7] ........................... B01J 27/14; B01J 27/186; B01J 27/187; B01J 27/199; B01J 23/00
(52) U.S. Cl. ....................... 502/208; 502/302; 502/303; 502/304
(58) Field of Search ............................... 502/302–304, 502/308, 208

(56) References Cited

U.S. PATENT DOCUMENTS

| 3,933,932 A | | 1/1976 | Vrieland et al. ......... 260/669 R |
| 5,045,289 A | * | 9/1991 | Fernando et al. ........... 423/21.1 |
| 5,057,627 A | | 10/1991 | Edwards ..................... 568/618 |
| 5,057,628 A | | 10/1991 | Edwards et al. ............. 568/618 |
| 5,059,719 A | | 10/1991 | Edwards ..................... 568/618 |
| 5,208,199 A | | 5/1993 | Kemp ........................ 502/208 |
| 5,210,325 A | | 5/1993 | Kemp et al. ................. 568/618 |
| 5,746,944 A | * | 5/1998 | Braconnier ........... 252/301.4 P |

FOREIGN PATENT DOCUMENTS

| JP | 57023674 | 2/1982 | ........... C09K/11/47 |

OTHER PUBLICATIONS

International Search Report of Jan. 5, 2004.
PCT Written Opinion for TH2234 PCT—International Patent Application No. PCT/US 03/26257.

* cited by examiner

*Primary Examiner*—Patricia L. Hailey

(57) ABSTRACT

A method of ensuring the production of efficient lanthanum phosphate catalysts (LAPO's) and rare earth phosphate catalysts (REPO's), and methods of alkoxylation using said efficient catalysts.

207 Claims, No Drawings

PREPARATION OF EFFICIENT REPO AND LAPO CATALYSTS

This application claims the benefit of U.S. Provisional Application No. 60/405,552 filed Aug. 23, 2002, the entire disclosure of which is hereby incorporated by reference.

FIELD OF THE INVENTION

The application relates to a method of ensuring the production of efficient lanthanum phosphate catalysts (LAPO's) and rare earth phosphate catalysts (REPO's).

BACKGROUND

Methods are always needed to ensure the production of catalysts with high activity toward catalyzing a particular reaction.

BRIEF SUMMARY

A method is provided for ensuring production of efficient rare earth metal phosphate catalysts for alkoxylation of organic compounds. The method comprises: selecting as a reactant one or more carbonate salts of the one or more rare earth metals; reacting the one or more carbonate salts with a source of phosphate under conditions effective to produce the efficient rare earth metal phosphate catalysts; wherein the efficient rare earth metal phosphate catalysts comprise an increased activity for the alkoxylation compared to the activity of substantially the same catalyst produced when one or more salts other than carbonate salts of the rare earth metals are selected as the reactant. Suitably, the increased activity for the alkoxylation is at least 1.5 times, preferably 2 times, more preferably 3 times, and most preferably 4 times the activity of substantially the same catalyst produced when one or more salts other than carbonate salts of the rare earth metals are selected as the reactant.

In one aspect, the phosphate catalyst comprises a lanthanum phosphate catalyst (LAPO). In another aspect, the phosphate catalyst comprises a rare earth metal selected from the group consisting of those having atomic numbers 39 and 57 through 71. In another aspect, the phosphate catalyst comprises a catalytically effective amount of one of the following groups: one or more of the phosphate salts of elements selected from the group consisting of cerium, lanthanum, praseodymium, neodymium, yttrium, samarium, gadolinium, dysprosium, erbium, and ytterbium; one or more of the phosphate salts of the cerium earth group elements; one or more of the phosphate salts of elements selected from the group consisting of cerium and lanthanum; one or more of the phosphate salts of the lanthanum elements (atomic numbers 57–71); one or more of the phosphate salts of the lanthanide series elements (atomic numbers 58–71); yttrium phosphate; one or more metals derived from natural mineral ores; one or more rare earth elements selected from the group consisting of bastnasite, monazite, xenotime, didymium, gadolinite and euxenite.

The conditions comprise mixing the one or more carbonate salts of the one or more rare earth metals with a volume of water to form a slurry. In one embodiment, the one or more carbonate salts comprise from about 8% to about 15% Ce, from about 44% to about 65% La, from about 20% to about 25% Nd, and from about 2% to about 10% Pr. In another embodiment, the one or more carbonate salts are the carbonates of the following metals in the following quantities: 12.5% w Ce, 59.3% w La, 22.4% w Nd and 5.8% w Pr.

The conditions further comprise preparing an aqueous solution of from about 5% to about 15% phosphoric acid with agitation at a temperature of from about 25° C. to about 80° C., preferably about 25° C. The conditions further comprise either (a) adding the carbonate slurry to the aqueous solution of phosphoric acid to produce a reaction mixture, or, preferably (b) adding the aqueous phosphoric acid to the carbonate slurry under slurrying conditions effective to produce a reaction mixture.

The slurrying conditions preferably comprise agitation at a temperature of from about 25° C. to about 100° C. and over a slurrying period of time sufficient to consume the carbonate. The slurrying period of time is from about 10 minutes to about 60 minutes, preferably about 30 minutes. The method preferably further comprises cooling the reaction mixture to a slurrying temperature effective to produce first solids; and subjecting the first solids to second slurrying conditions effective to separate the first solids from the reaction mixture and to form an aqueous second slurry comprising the first solids. The second slurrying conditions preferably comprise stirring at a temperature of from about 25° C. to about 80° C., preferably about 50° C., for from about 10 minutes to about 60 minutes, preferably about 30 minutes, to produce a heated second slurry.

The method preferably further comprises cooling the heated second slurry, preferably to about 25° C., producing a cooled second slurry comprising second solids; and, subjecting the second solids to neutralizing conditions effective to neutralize the mixture, producing a neutralized second slurry comprising neutralized solids. The neutralizing conditions preferably comprise adding aqueous $NH_4OH$. The method preferably further comprises cooling the neutralized second slurry, preferably to about 25° C., and collecting the neutralized solids. The method preferably further comprises drying the neutralized solids to produce a cake comprising the one or more phosphate salts. The method also preferably further comprises grinding the cake to produce a free flowing powder.

The application also provides a method comprising reacting alkylene oxides and organic compounds comprising active hydrogen in the presence of a catalytically effective amount of a carbonate salt derived catalyst made according to the foregoing methods. The alkylene oxides preferably comprise one or more vicinal alkylene oxides. The catalytically effective amount of carbonate salt derived catalyst typically is about 0.006% w or more, more typically about 0.013 to about 3.33% w or more, even more typically from about 0.067 to about 1.33% w or more. In another aspect, the catalytically effective amount of a carbonate salt derived catalyst is about 0.0025% w or more, more typically from about 0.005 to about 1.25% w or more, even more typically from about 0.025 to about 0.5% w or more.

Stated another way, if a quantity (x) of a carbonate derived catalyst of a given rare earth or lanthanum series metal or mixture is used, and the same quantity (x) of the same catalyst which is not carbonate derived is used to catalyze a reaction under the same conditions, then the reaction time for the reaction catalyzed by the carbonate-derived catalyst will be about ⅔ or less, preferably about ½ less, more preferably about ¼ or less the reaction time required to achieve the same level of catalysis by the non-carbonate salt derived catalyst.

The organic compound comprises active hydrogen. In a preferred embodiment, the active hydrogen comprises a primary active hydrogen. Suitably, the organic compound is one or more compound selected from the group consisting of alkanols, phenols, thiols, amines, polyols, and carboxylic acids.

In one aspect, the carboxylic acids are selected from the group consisting of mono- and dicarboxylic acids, both aliphatic (saturated and unsaturated) and aromatic. In another aspect, the carboxylic acid is selected from the group consisting of acetic acid, propionic acid, butyric acid, valeric acid, caproic acid, lauric acid, myristic acid, palmitic acid, stearic acid, oleic acid, rosin acids, tall oil acids, terephthalic acid, benzoic acid, phenylacetic acid, toluic acid, acrylic acid, methacrylic acid, crotonic acid, and maleic acid;

In another aspect, the amines preferably are selected from the group consisting of primary, secondary, and tertiary alkylamines, and alkylamines containing both amino and hydroxyl groups, such as N'N-di(n-butyl)-ethanol amine and tripropanolamine.

In another aspect, the thiols are selected from the group consisting of primary, secondary, and tertiary alkane thiols having from 1 to about 30 carbon atoms, particularly those having from about 8 to about 20 carbon atoms. Where the thiol is a tertiary thiol, the tertiary thiol suitably comprises a branched carbon chain derived via hydrosulfurization of the products of the oligomerization of lower olefins, particularly the dimers, trimers, and tetramers and pentamers of propylene and the butylenes. Where the thiol is a secondary thiol, suitable secondary thiols are selected from the group consisting of lower alkane thiols, such as 2-propanethiol, 2-butanethiol, and 3-pentanethiols, and the products of the hydrosulfurization of the substantially linear oligomers of ethylene as are produced by the Oxo process. Where the thiol is a primary thiol, suitable thiols are selected from the group consisting of 2-decanethiol, 3-decanethiol, 4-decanethiol, 5-decanethiol, 3-dodecanethiol, 5-dodecanethiol, 2-hexadecanethiol, 5-hexadecanethiol, and 8-octadencanethiol, 2-methyl-4-tridecanethiol, 1-butanethiol, 1-hexanethiol, 1-dodecanethiol, 1-tetradecanethiol and 2-methyl-1-tridecanethiol.

In another aspect, the polyols have from about 2 to about 30 carbon atoms and from about 2 to about 6 hydroxyl groups. In one aspect, the polyol is selected from the group consisting of alkylene glycols and polyalkylene glycol ethers. In another aspect, the polyol is selected from the group consisting of ethylene glycol, propylene glycol, hexylene glycol, and decylene glycol, diethylene glycol, triethylene glycol, propylene glycol, dipropylene glycol, tripropylene glycol, glycerine, and sorbitol.

In yet another aspect, the phenols are selected from the group consisting of phenol and of alkyl-substituted phenols comprising alkyl substituents having from one to about 30 (preferably from one to about 20) carbon atoms. In another aspect, suitable phenols are selected from the group consisting of p-methylphenol, p-ethylphenol, p-hexylphenol, nonylphenol, p-decylphenol, and didecyl phenol.

In even another aspect, the organic compound is one or more acyclic aliphatic mono-hydric alkanols having from about 1 to about 30 carbon atoms, preferably from about 6 to about 24 carbon atoms, more preferably from about 8 to about 20 carbon atoms. In another aspect, the alkanols comprise greater than about 50 percent, more preferably greater than about 60 percent and most preferably greater than about 70 percent molecules having a linear (straight-chain) carbon structure.

In yet another aspect, the organic compound is the alkoxylate product of a previous alkoxylation of an active hydrogen containing compound.

In a preferred embodiment, the alkylene oxide is selected from the group consisting of ethylene oxide, propylene oxide, and mixtures thereof.

In another preferred embodiment, the alkylene oxide is ethylene oxide and the organic compound is a $C_1$ to $C_{30}$ primary alkanol. In this aspect, the catalyst preferably consists essentially of salts having the formula $LPO_4$.

DETAILED DESCRIPTION

The present application provides a method to ensure the production of lanthanum phosphate catalysts (LAPO's) and rare earth phosphate catalysts (REPO's) which are highly efficient at catalyzing alkoxylation processes. Specifically, the method involves selecting a particular salt of the lanthanum or rare earth metal—namely, the carbonate salt—as the reactant to be treated with a phosphate.

The catalyst comprises the phosphate salt(s) of either one or a mixture of the rare earth elements. As used herein, the "rare earth metals" are those of atomic numbers 39 and 57 through 71, metals of the "lanthanum series" are those of atomic numbers 57 through 71; the "lanthanide" metals are those of atomic numbers 58 through 71. Traditionally, the lanthanum metals have further been divided into the "cerium earth" group of atomic numbers 57 through 62, the "terbium earth" group of atomic numbers 63 through 66, and the "yttrium earth" group of atomic numbers 67 through 71 (so named not because yttrium is a member of the group, but because yttrium is found with these elements in nature).

In one respect, preference can be expressed for catalysts comprising in catalytically effective amount one or more of the phosphate salts of elements selected from the group comprising cerium, lanthanum, praseodymium, neodymium, yttrium, samarium, gadolinium, dysprosium, erbium, and ytterbium. In another respect, catalysts comprising a catalytically effective amount of one or more of the phosphate salts of the cerium earth group elements are particularly preferred, while catalysts comprising a catalytically effective amount of one or more of the phosphate salts of elements selected from the group consisting of cerium and lanthanum are considered most preferred. In a further respect, preferred catalysts comprise a catalytically effective amount of one or more of the phosphate salts of the lanthanum elements (atomic numbers 57—71). Still further, a preferred class of catalysts comprise a catalytically effective amount of one or more of the phosphate salts of the lanthanide series elements (atomic numbers 58—71). In still another respect, preference can be expressed for catalysts comprising yttrium phosphate in catalytically effective amounts.

Natural mineral ores which serve as the commercial sources of the rare earth elements generally contain several of the elements. These ores are often refined without separating this mixture into distinct elements. For this reason, the use of mixtures of the phosphate salts of several rare earth elements may be preferred from the standpoint of availability and cost. Specific examples of suitable mixtures of rare earth elements include those known as bastnasite, monazite, xenotime, didymium, gadolinite and euxenite.

In addition to a catalytically effective amount of the rare earth element compounds, the catalyst also may suitably contain other substances, including both those which may be introduced into the process as impurities in the phosphate salt catalyst as well as those which may be added to promote or modify catalyst activity.

The phosphate salt catalyst compounds are suitably characterized by the formula $L_p(PO_4)_q$, wherein L is a rare earth element. The phosphate salts of the rare earth elements principally comprise rare earth elements in the trivalent state and have the formula $LPO_4$. However, the process encompasses divalent metal salts and tetravalent metal salts, in which case the subscripts p and q satisfy the relevant valency relationships, that is, when L is divalent p is 3 and q is 2, and when L is tetravalent p is 3 and q is 4.

Phosphate salt compounds of the rare earth elements are effective catalysts for the addition reactions of alkylene oxides with organic compounds having active hydrogen atoms. Basically, an alkylene oxide reactant comprising one or more vicinal alkylene oxides is contacted with an active hydrogen reactant comprising one or more organic compounds (e.g., alcohols, phenols, thiols, amines, polyols, carboxylic acids, etc.) having one or more active hydrogen atoms, in the presence of a catalyst comprising one or more of the phosphate salts of the rare earth elements.

In a preferred embodiment, the rare earth phosphate catalyst is prepared as follows. A quantity of a rare earth carbonate mixture is added to a volume of water to form a slurry. The water preferably is distilled, more preferably distilled and degassed. A suitable rare earth carbonate mixture comprises at least La carbonate and preferably comprises one or more of Ce carbonate, Nd carbonate, and Pr carbonate. A most preferred carbonate mixture comprises from about 8% to about 15% Ce, from about 44% to about 65% La, from about 20% to about 25% Nd, and from about 2% to about 10% Pr. A preferred commercially available carbonate mixture is Unical 76 (lot#R-1220), which comprises metallic composition of 12.5% w Ce, 59.3% w La, 22.4% w Nd and 5.8% Pr.

An aqueous solution of phosphoric acid is prepared at a concentration of from about 5% to about 15%. The water used in the solution also is preferably distilled, most preferably distilled and degassed. The solution is stirred rapidly at a temperature of from about 25° C. to about 80° C., preferably about 25° C.

It is possible to either add the carbonate slurry to the phosphoric acid or to add the phosphoric acid to the slurry. Preferably, the phosphoric acid is added to the slurry with agitation at a temperature of from about 25° C. to about 100° C. and over a period of time sufficient to consume the carbonate. The period of time typically is from about 10 minutes to about 60 minutes, preferably about 30 minutes. The reaction mixture is then heated to reflux (~100C.) while stirring rapidly for a period of time effective to consume all carbonate, typically from about 1 to about 3 hours, preferably about 2.5 hours. The heat is removed, the stirring is stopped, and the reaction mixture is allowed to cool, preferably to room temperature, or about 25° C. The solids are filtered and then transferred again to the reaction vessel wherein they are diluted with an excess of water, preferably degassed distilled water, to form a slurry. The slurry is stirred while maintained at a temperature of from about 25° C. to about 80° C., preferably about 50° C., for from about 10 minutes to about 60 minutes, preferably about 30 minutes. The heat is removed and the mixture is allowed to cool to room temperature, or about 25° C. The solids are filtered and treated with a solution of aqueous base in an amount and at a concentration effective to neutralize the mixture. A preferred aqueous base is $NH_4OH$, most preferably about 10 N $NH_4OH$.

The resulting slurry is stirred with heating for a time and at a temperature effective to neutralize all acid. Suitable temperatures are from about 25° C. to about 80° C., preferably about 50° C. A suitable time is from about 10 minutes to about 60 minutes, preferably about 30 minutes. The heat is removed and the mixture is allowed to cool to room temperature, or about 25° C. The solids are filtered and dried using any suitable drying technique. In a preferred embodiment, the solids are dried overnight at room temperature under vacuum, and then dried further by heating under full vacuum for an effective drying period. Suitable temperatures for this heating are from about 25° C. to about 80° C., preferably about 50° C. The drying period will vary depending upon the conditions, but suitably is from about 4 to about 10 hours, preferably about 8 hours. The resulting product is collected as a cake, ground using any suitable technique, such as a mortar and pestle, to produce a free flowing off white powder comprising one or more of the phosphate salts of the rare earth elements.

A catalytically effective amount of the powder is used in an alkoxylation reaction. A catalytically effective amount is an amount sufficient to cause the H-containing compound to react with ethylene or propylene oxide. The catalyst made according to the present method are 1.5 or more times as active, typically 2 or more times as active, preferably from about 2 to about 4 times as active as the same catalyst prepared using non-carbonate salts of rare earth metals. The more active catalyst made using carbonate salts may be used to achieve a savings in time and/or cost.

A catalytically effective amount of a non-carbonate derived salt typically is about 0.01 percent or more by weight (% w), more typically from about 0.02 to about 5% w, even more typically from about 0.1 to about 2% w. These percentages are in terms of the weight of rare earth metal ions in the process mixture relative to the weight of active hydrogen containing compounds in that mixture. Substantially greater quantities of catalyst, e.g., up to about 10% w or more, are also suitable.

In contrast, under the same conditions of reaction, a catalytically effective amount of a carbonate salt derived catalyst typically is about 0.006% w or more, more typically about 0.013 to about 3.33% w or more, even more typically from about 0.067 to about 1.33% w or more. In a preferred embodiment, under the same conditions of reaction, a catalytically effective amount of a carbonate salt derived catalyst is about 0.005% w or more, more typically from about 0.01 to about 2.5% w or more, and even more typically from about 0.5 to about 1% w or more. In a most preferred embodiment, under the same conditions of reaction, a catalytically effective amount of a carbonate salt derived catalyst is about 0.0025% w or more, more typically from about 0.005 to about 1.25% w or more, even more typically from about 0.025 to about 0.5% w or more.

Alternately, if a quantity (x) of a carbonate derived catalyst of a given rare earth or lanthanum series metal or mixture is used, and the same quantity (x) of the same catalyst which is not carbonate derived is used to catalyze a reaction under the same conditions, then the reaction catalyst by the carbonate-derived catalyst will take about ⅔ or less, preferably about ½ or less, more preferably about ¼ or less of the reaction time required to achieve the same level of catalysis by the non-carbonate salt derived catalyst.

In the alkoxylation processes catalyzed, alkylene oxides are reacted with compounds having active hydrogen atoms in the presence of catalysts comprising one or more carbonate derived phosphate salts of lanthanum or the rare earth elements. The preparation of an alkanol ethoxylate (represented by formula III below) by addition of a number (n) of ethylene oxide molecules (formula II) to a single alkanol molecule (formula I) is represented by the equation

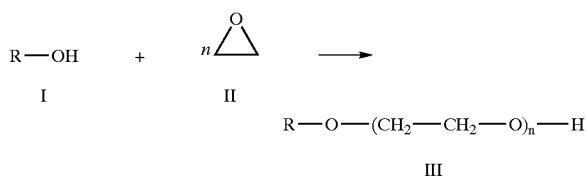

A large variety of products useful, for instance, as nonionic surfactants, wetting and emulsifying agents,. solvents, and chemical intermediates, are prepared by the addition reaction (alkoxylation reaction) of alkylene oxides (epoxides) with organic compounds having one or more active hydrogen atoms. Examples include, but are not necessarily limited to alkanol ethoxylates and alkyl-substituted phenol ethoxylates prepared by reacting ethylene oxide with aliphatic alcohols or substituted phenols having from about 6 to about 30 carbon atoms. Ethoxylates, and to a lesser extent corresponding propoxylates and compounds containing mixed oxyethylene and oxypropylene groups, are widely employed as nonionic detergent components of commercial cleaning formulas used in industry and in the home. The addition reaction of propylene oxide with polyols provides intermediates for the preparation of polyurethane products. In preferred embodiments, the alkoxylate products are useful as nonionic surfactants.

Preferably, the alkoxylation process minimizes the quantity of unreacted (or residual) active hydrogen reactant remaining in the final product. A high level of residual reactant either represents a loss of valuable reactant, or requires that further processing of the product be carried out to recover the reactant. Moreover, the presence of the unreacted material is often a disadvantage from the standpoint of product quality and environmental concerns. For instance, residual alkanol in a detergent alcohol ethoxylate product contributes to volatile organic emissions during spray drying of detergent formulations.

The rare earth phosphate salts are present in the alkoxylation mixture in catalytically effective amount in either (or both) homogeneous or heterogeneous form(s). The catalyst has been found to be heterogeneous, or at least essentially heterogeneous, in preferred embodiments. The process, as a general rule, suitably is conducted using such reactants and practicing under such processing procedures and reaction conditions as are well known in the art for alkoxylation reactions. Certain preferences may, however, be expressed for particular reactants, procedures and conditions.

Thus, for instance, the invention is preferably applied to processes utilizing an alkylene oxide (epoxide) reactant which comprises one or more vicinal alkylene oxides, particularly the lower alkylene oxides and more particularly those in the $C_2$ to $C_4$ range.

Likewise, the active hydrogen reactants suitably utilized in the process of the invention include those known in the art for reaction with alkylene oxides and conversion to alkoxylate products. Suitable classes of active hydrogen reactants include (but are not necessarily limited to) alcohols, phenols, thiols (mercaptans), amines, polyols, carboxylic acids, and mixtures thereof. Generally, but not necessarily, the active hydrogen moiety of the reactant is of the form—XH wherein X represents either an oxygen, sulfur or (substituted, e.g., amino) nitrogen atom. Preference generally exists for use of hydroxyl-containing reactants. More preferably, the active hydrogen-containing reactant consists essentially of one or more active hydrogen containing compounds selected from the group consisting of alkanols, alkyl polyols and phenols (including alkyl-substituted phenols).

Preference can also be expressed for the application of this invention to the alkoxylation of primary active hydrogen containing compounds, that is, compounds wherein the active hydrogen moiety is attached to a primary carbon atom. As is often the case for alkoxylation reactions, such primary compounds are more reactive, and in some cases substantially more reactive, in the process of this invention than are the corresponding secondary and tertiary compounds. Moreover, the invention has been found to produce relatively broad-range alkylene oxide adduct distribution products when applied to secondary and tertiary active hydrogen containing reactants.

Among the suitable carboxylic acids, particular mention may be made of the mono- and dicarboxylic acids, both aliphatic (saturated and unsaturated) and aromatic. Specific examples include acetic acid, propionic acid, butyric acid, valeric acid, caproic acid, lauric acid, myristic acid, palmitic acid, stearic acid, oleic acid, rosin acids, tall oil acids, terephthalic acid, benzoic acid, phenylacetic acid, toluic acid, acrylic acid, methacrylic acid, crotonic acid, maleic acid, and the like. It has been observed that, as a rule, carboxylic acids undergo alkoxylation in the process of this invention at a relatively slow rate.

Among the suitable amines, particular mention may be made of primary. secondary and tertiary alkylamines and of alkylamines containing both amino and hydroxyl groups, e.g., N'N-di(n-butyl)-ethanol amine and tripropanolamine.

Among the suitable thiols, particular mention may be made of primary, secondary and tertiary alkane thiols having from 1 to about 30 carbon atoms, particularly those having from about 8 to about 20 carbon atoms. Specific examples of suitable tertiary thiols are those having a highly branched carbon chain which are derived via hydrosulfurization of the products of the oligomerization of lower olefins, particularly the dimers, trimers, and tetramers and pentamers of propylene and the butylenes. Secondary thiols are exemplified by the lower alkane thiols, such as 2-propanethiol, 2-butanethiol, and 3-pentanethiols, as well as by the products of the hydrosulfurization of the substantially linear oligomers of ethylene as are produced by the Oxo process. Representative, but by no means limiting, examples of thiols derived from ethylene oligomers include the linear carbon chain products, such as 2-decanethiol, 3-decanethiol, 4-decanethiol, 5-decanethiol, 3-dodecanethiol, 5-dodecanethiol, 2-hexadecanethiol, 5-hexadecanethiol, and 8-octadencanethiol, and the branched carbon chain products, such as 2-methyl-4-tridecanethiol. Primary thiols are typically prepared from terminal olefins by hydrosulfurization under free-radical conditions and include, for example, 1-butanethiol, 1-hexanethiol, 1-dodecanethiol, 1-tetradecanethiol and 2-methyl-1-tridecanethiol.

Among the polyols, particular mention may be made of those having from 2 to about 6 hydroxyl groups. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like.

The alcohols (both mono- and poly-hydroxy) and the phenols (including alkyl-substituted phenols) are preferred classes of active hydrogen reactants for purposes of the invention. Among the phenols, particular mention may be made of phenol and of alkyl-substituted phenols wherein each alkyl substituent has from one to about 30 (preferably from one to about 20) carbon atoms, for example, p-methylphenol, p-ethylphenol, p-hexylphenol, nonylphenol, p-decylphenol, didecyl phenol and the like.

Acyclic aliphatic mono-hydric alcohols (alkanols) form a most preferred class of reactants, particularly the primary alkanols, although secondary and tertiary alkanols are also very suitably utilized in the process of the invention. Preference can also be expressed, for reason of both process performance and commercial value of the product, for alkanols having from 1 to about 30 carbon atoms, with $C_6$ to $C_{24}$ alkanols considered more preferred and $C_8$ to $C_{20}$ alkanols considered most preferred. As a general rule, the alkanols may be of branched or straight chain structure, although preference further exists for alkanol reactants in which greater than about 50 percent, more preferably greater than about 60 percent and most preferably greater than about 70 percent of the molecules are of linear (straight-chain) carbon structure.

The general suitability of such alkanols as reactants in alkoxylation reactions is well recognized in the art. Commercially available mixtures of primary mono-hydric alkanols prepared via the oligomerization of ethylene and the hydroformylation or oxidation and hydrolysis of the resulting higher olefins are particularly preferred. Examples of commercially available alkanol mixtures include the NEODOL Alcohols, trademark of and sold by Shell Chemical Company, including mixtures of $C_9$, $C_{10}$ and $C_{11}$ alkanols (NEODOL 91 Alcohol), mixtures of $C_{12}$ and $C_{13}$ alkanols (NEODOL 23 Alcohol), mixtures of $C_{12}$, $C_{13}$, $C_{14}$, and $C_{15}$ alkanols (NEODOL 25 Alcohol), and mixtures of $C_{14}$ and $C_{15}$ alkanols (NEODOL 45 Alcohol); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418); and the TERGITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Proctor and Gamble Company and the TA alcohols of Ashland Oil Company.

Among the polyols, particular mention may be made of those having from 2 to about 6 hydroxyl groups and 2 or more, preferably 2 to 30 carbon atoms. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like. Higher oligomers and polymers of the polyols are also very suitable.

The active hydrogen containing reactant is also very suitably the alkoxylate product of a previous alkoxylation of an active hydrogen containing compound.

Persons of ordinary skill in the art will be familiar with additional examples of both specific alkylene oxide reactants and specific active hydrogen containing reactants suitable for use in the present process.

In preferred embodiments, the alkylene oxide reactant is ethylene oxide or propylene oxide or a mixture of ethylene oxide and propylene oxide and the active hydrogen containing reactant is an alcohol, a polyol or another hydroxyl containing compound in the presence of a catalytically effective amount of the rare earth phosphate salt catalyst. In a particularly preferred embodiment, ethylene oxide is contacted and reacted with a $C_1$ to $C_{30}$ primary alkanol in the presence of acatalytically effective amount of a catalyst wherein the rare earth phosphate compounds consist essentially of salts having the formula $LPO_4$.

In terms of processing procedures, the alkoxylation reaction in the invention may be conducted in a generally conventional manner. For example, the catalyst may initially be mixed with liquid active hydrogen reactant. The mixture of catalyst and liquid reactant is contacted, preferably under agitation, with alkylene oxide reactant, which is typically introduced in gaseous form, at least for the lower alkylene oxides. The order in which the reactants and catalyst are contacted has not been found to be critical to the invention.

While these procedures describe a batch mode of operation, the invention is equally applicable to a continuous process.

The catalyst is either soluble (either partially or completely) or insoluble in this liquid reactant as well as in liquid mixtures of the reactant and the product formed as the process is carried out. The catalyst is insoluble, or at least essentially insoluble, in the preferred active hydrogen containing reactants, particularly in primary alcohols and the products of their alkoxylation. While it is not intended to limit the scope of the invention to one theory or mechanism of operation, it is believed that the presence of phosphate salts in a hexagonal crystal structure in the alkoxylation mixture, particularly in alkanol alkoxylation mixtures, may have a beneficial influence on reaction rate and adduct distribution. Salts in the monoclinic form have been observed in some cases to be less active than the salts in the hexagonal form. Preference has also been observed for use of phosphate salts having a certain water content associated with their crystal structure, particularly a water content of greater than about 5% w (e.g., 5–20% w), although the amount of water contained in the phosphate salt is not considered critical to the alkoxylation.

Overall, the two reactants are utilized in quantities which are predetermined to yield an alkoxylate product of the desired mean or average adduct number. The average adduct number of the product is not critical to this process. Such products commonly have an average adduct number in the range from less than one to about 30 or greater.

In general terms, suitable and preferred process temperatures and pressures for purposes of this invention are the same as in conventional alkoxylation reactions between the same reactants, employing conventional catalysts. A temperature of at least about 90° C., particularly at least about 120° C. and most particularly at least about 130° C., is typically preferred from the standpoint of the rate of reaction, while a temperature of about 250° C. or less, particularly about 210° C. or less, and most particularly about 190° C. or less, typically is desirable to minimize degradation of the product. As is known in the art, the process temperature can be optimized for given reactants, taking such factors into account.

Superatmospheric pressures, e.g., pressures between about 10 and 150 psig, are preferred, with pressure being sufficient to maintain the active hydrogen reactant substantially in the liquid state.

When the active hydrogen reactant is a liquid and the alkylene oxide reactant is a vapor, alkoxylation is then suitably conducted by introducing alkylene oxide into a pressure reactor containing the liquid active hydrogen reactant and the catalyst. For considerations of process safety, the partial pressure of a lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known in the art, are taken to manage the risks of explosion. A total pressure of from about 40 to about 110 psig, with an alkylene oxide partial pressure of from about 15 to about 60 psig, is particularly preferred, while a total pressure of from about 50 to about 90 psig, with an alkylene oxide partial pressure of from about 20 to about 50 psig, is considered more preferred.

The time required to complete a process according to the invention is dependent both upon the degree of alkoxylation desired (i.e., upon the average alkylene oxide adduct number of the product) as well as upon the rate of the alkoxylation reaction (which is, in turn, dependent upon temperature, catalyst quantity and nature of the reactants). A typical reaction time for preferred embodiments is from about 1 to about 24 hours.

After the ethoxylation reaction has been completed, the product preferably is cooled. If desired, catalyst can be removed from the final product, although catalyst removal is not necessary to the process of the invention. Catalyst residues may be removed, for example, by filtration, precipitation, extraction, or the like. A number of specific chemical and physical treatment methods have been found to facilitate removal of catalyst residues from a liquid product. Such treatments include contact of the alkoxylation product with strong acids such as phosphoric and/or oxalic acids or with solid organic acids such as NAFION H+ or AMBERLITE IR 120H; contact with alkali metal carbonates and bicarbonates; contact with zeolites such as Type Y zeolite or mordenite; or contact with certain clays. Typically, such treatments are followed by filtration or precipitation of the solids from the product. In many cases filtration, precipitation, centrifugation, or the like, is most efficient at elevated temperature.

Alkoxylation product mixtures prepared under the present invention are of high quality and have greater stability, relative to the product mixtures of acid or base catalyzed alkoxylation reactions. In this regard, the invention is particularly useful for the preparation of colorless or less colored product relative to those of conventional practice, because the neutral salts do not promote degradation reactions which lead to color forming impurities.

The following Examples are provided to further illustrate certain specific aspects of the invention but are not intended to limit its broader scope.

EXAMPLE 1

Lanthanum and rare earth metal phosphate catalysts (LAPO's and REPO's, respectively) were made using a variety of lanthanum and rare earth metal salts as precursors. The following were the salts from which the catalysts were derived:

| Sample: | Salt: |
|---|---|
| A: | nitrate |
| B: | carbonate |
| C: | carbonate |
| D: | carbonate |
| E: | carbonate |
| F: | carbonate |
| G: | carbonate |

The following were the results:

The Amount of Alkoxylated Product Produced

| Time | A | B | C | D | E | F | G |
|---|---|---|---|---|---|---|---|
| 0 | 0 | 0 | 0 | 0 | 0 | 0 | 0 |
| 1 | | | | 22 | | 13 | 18 |
| 2 | 4 | 23 | | | | 34 | 33 |
| 3 | | | | 51 | 47 | 39 | 56 |
| 4 | | 32 | 38 | 67 | | 49 | |
| 5 | | 49 | 49 | | | | 72 |
| 6 | 25 | 70 | 54 | 84 | 61 | 61 | |
| 7 | 35 | 88 | 62 | | | 71 | 85 |
| 8 | 50 | | 73 | 105 | 82 | 76 | 93 |
| 9 | | | 94 | | 92 | | 105 |
| 10 | | | | | 100 | 85 | |
| 11 | 61 | 116 | 106 | 115 | 109 | 95 | |
| 12 | | 123 | | | | 102 | 117 |
| 13 | 73 | | 116 | 122 | 120 | | |
| 14 | | | 127 | | | | 131 |
| 15 | 80 | 140 | | | 128 | | 138 |
| 16 | | | | 141 | | 124 | |
| 17 | | | 150 | | 144 | 132 | |
| 18 | | | | 148 | | | 151 |
| 19 | | | 158 | | 155 | 137 | |
| 20 | | | 166 | | | | 157 |
| 21 | | | | 159 | 167 | 147 | 161 |
| 22 | | | | | | | |
| 23 | 105 | 158 | 178 | | 175 | 152 | 174 |
| 24 | | | 183 | 173 | 181 | | 179 |
| 25 | | 172 | 193 | 178 | 189 | 156 | |
| 26 | | | 196 | | | 166 | 186 |
| 27 | | | 201 | | | | 191 |
| 28 | 112 | 196 | | 189 | 198 | 174 | 197 |
| 29 | | | | | 200 | | |
| 30 | | | | 197 | | | 200 |
| 31 | | | | | | 183 | |
| 32 | | | | | | | |
| 33 | | | | 201 | | 191 | |
| 34 | | 200 | | | | | |
| 35 | | | | | | | |
| 36 | | | | | | 200 | |
| 48 | 133 | | | | | | |
| 55 | 138 | | | | | | |
| 58 | 145 | | | | | | |
| 61 | 153 | | | | | | |
| 64 | 170 | | | | | | |
| 75 | 183 | | | | | | |
| 78 | 191 | | | | | | |
| 85 | 200 | | | | | | |

The catalysts derived from carbonate salts were 2–3 times more active than the catalysts derived from other salts.

EXAMPLE 2

A number of lanthanum and rare earth phosphate catalysts were prepared for comparison of their catalytic activity in alkoxylation reactions. The procedures used to prepare the catalysts were as follows:

A. Lanthanum Phosphate Catalyst Prepared from Lanthanum Nitrate (LAPO 1)

A supplier was instructed to prepare lanthanum phosphate catalyst from lanthanum nitrate using the following procedures:

Dissolve 20 grams (0.046 moles) of lanthanum nitrate hexahydrate in 100 ml of $N_2$ purged distilled $H_2O$. Prepare an aqueous phosphoric acid solution by dissolving 5.3 g of 85% phosphoric acid (0.046 moles) in 50 grams of distilled $H_2O$. Add the lanthanum altrate solution to the phosphoric acid solution at 25° C. in a 500 ml round bottom flask equipped with overhead stirrer, reflux condenser, $N_2$ sparge inlet and thermocouple. Heat the white precipitate to 100° C. for 3 hours. Remove the heat, stop the stirring, and allow the reaction mixture to cool to 25° C. Again filter and transfer the solids to the reaction vessel. Add 100 ml of $N_2$ degassed distilled $H_2O$ to the wet white powder, and stir the slurry at 50° C. for 30 minutes. Remove the heat and allow the mixture to cool to 25° C. Filter and treat the solids with a solution containing 5 ml of 10N $NH_4OH$ dissolved in 100 ml of water. Stir this slurry at 50° C. for 30 minutes. Remove the heat and allow the mixture to cool to 25° C. Filter the solids and allow the filtered solids to dry overnight at 25° C. under vacuum. Dry the solids further by heating under full vacuum at 50° C. for 8 hours. Collect the product as a cake, grind with a mortar and pestle, producing 13.9 grams of a free flowing off white powder.

B. Rare Earth Phosphate Catalyst 1 (REPO 1)

A mixed rare earth phosphate catalyst (REPO 1) was prepared according to the following procedures: 312.6 g (0.68 moles) of a rare earth carbonate mixture obtained from Unical 76 (lot#R-1220), consisting of a metallic composition of 12.5% w Ce, 59.3% w La, 22.4% w Nd and 5.8% Pr was added to 2000 ml $N_2$ degassed distilled $H_2O$. A solution of aqueous phosphoric acid was prepared by dissolving 165 g of 85% $H_3PO_4$ (1.43 moles) in 2000 ml of $N_2$ degassed distilled $H_2O$ contained in a 12 liter reaction flask equipped with overhead stirrer, reflux condenser, $N_2$ sparge inlet and thermocouple. The reaction solution was stirred rapidly at 25° C. at which time the aqueous rare earth carbonate slurry was added over a 30 minute period. The reaction mixture was then heated to reflux (~100° C.) while stirring rapidly for a period of 2.5 hours. Heat was removed and stirring stopped. The reaction was allowed to cool to 25° C. The solids were filtered and then transferred again to the reaction vessel. 5000 ml of $N_2$ degassed distilled $H_2O$ was added to the wet white powder, and the slurry was allowed to stir at 50° C. for 30 minutes. The heat was removed and the mixture was allowed to cool to 25° C. The solids were filtered and treated again with a solution containing 100 ml of 10N $NH_4OH$ dissolved. This slurry was allowed to stir at 50° C. for 30 minutes. The heat was removed and the mixture was allowed to cool to 25° C. The solids were filtered and allowed to dry overnight at 25° C. under vacuum. The solids were dried further by heating under full vacuum at 50° C. for 8 hours. The product was collected as a cake, ground with a mortar and pestle producing 286 grams of a free flowing off white powder.

C. Rare Earth Phosphate Catalyst 2 (REPO 2)

A mixed rare earth phosphate catalyst was prepared in the same manner as REPO 1 except on $\frac{1}{10}^{th}$ the scale, and the rare earth carbonate mixture was prepared in the laboratory using pure single metal carbonates: a mixture of rare earth carbonates was prepared by mixing 3.9 g of cerium carbonate hydrate, 18.5 g of lanthanum carbonate hydrate, 7.0 g of neodymium carbonate hydrate and 1.8 g of praseodymium carbonate hydrate. This mixture (31.2 g, 0.068 moles) was added to 200 ml. of $N_2$ degassed distilled $H_2O$. A solution of aqueous phosphoric acid was prepared by dissolving 16.5 g of 85% $H_3PO_4$ (0.143 moles) in 200 ml of $N_2$ degassed distilled $H_2O$ contained in a 1000 ml round bottom flask equipped with overhead stirrer, reflux condenser, $N_2$ sparge inlet and thermocouple. The reaction solution was stirred rapidly at 25° C. at which time the aqueous rare earth carbonate slurry was added over a 15 minute period. The reaction mixture was then heated to reflux (~100° C.) while stirring rapidly for a period of 3 hours. Heat was removed and stirring stopped. The reaction was allowed to cool to 25° C. The solids were filtered and then transferred again to the reaction vessel. 500 ml of $N_2$ degassed distilled $H_2O$ was added to the wet white powder, and the slurry was allowed to stir at 50° C. for 30 minutes. The heat was removed and the mixture was allowed to cool to 25° C. The solids were filtered and treated again with a solution containing 10 ml of 10N $NH_4OH$ dissolved in 500 ml of water. This slurry was allowed to stir at 50° C. for 30 minutes. The heat was removed and the mixture was allowed to cool to 25° C. The solids were filtered and allowed to dry overnight at 25° C. under vacuum. The solids were dried further by heating under full vacuum at 50° C. for 8 hours. The product was collected as a cake, ground with a mortar and pestle producing 32 grams of a free flowing off white powder. This catalyst was evaluated as REPO 2.

D. Rare Earth Phosphate Catalyst 3 (REPO 3)

The procedures in paragraph C were repeated exactly producing another mixed rare earth phosphate catalyst with the same composition of rare earth metals as REPO 1. This catalyst was evaluated as REPO 3.

E. Lanthanum Phosphate Catalyst (LAPO 2)

A lanthanum phosphate catalyst was prepared according to the procedures used in paragraph C except that 31.2 grams (0.068 moles) of lanthanum carbonate hydrate was used instead of the rare earth phosphate mixture. This catalyst was evaluated as LAPO 2.

F. Lanthanum Phosphate Catalyst (LAPO 3)

The procedure in paragraph C was repeated exactly producing another lanthanum phosphate catalyst. This catalyst evaluated as LAPO 3.

G. Rare Earth Phosphate Catalyst (REPO 4)

The procedure in paragraph C was repeated exactly producing another mixed rare earth phosphate catalyst with the same composition of rare earth metals as in paragraph C. This catalyst evaluated as REPO 4.

The foregoing catalysts were used to catalyze alkoxylation according to the following protocol:

General Protocol for the Evaluation of Lanthanum or Rare Earth Phosphate Ethoxylation Catalysts In the following Examples, the ethoxylations were conducted under the following procedures. The alkylene oxide reactant for this process embodiment consisted of ethylene oxide and the active hydrogen containing reactant consisted of NEODOL 23 Alcohol (NEODOL is a trademark of Shell Chemical Company) characterized as a mixture of primary, 80% linear (20% branched), alkanols having twelve and thirteen carbon atoms (about 40% by mol $C_{12}$ and 60% by mol $C_{13}$).

Initially, 0.5 grams of the powder prepared as described above was added to 125 grams (0.644 moles) of NEODOL 23 Alcohol which had been predried under a $N_2$ sparge for 2 hours at 125° C. to drive off water. The resulting slurry was transferred to a 500 ml autoclave reactor maintained under nitrogen atmosphere. The temperature of the reactor and contents was raised to 160° C. A mixture of nitrogen and ethylene oxide was then introduced into the reactor to a total pressure of 75 psia (45 psia nitrogen and 30 psia ethylene oxide). Alkoxylation (ethoxylation) commenced immediately. Additional ethylene oxide was supplied on demand to maintain an essentially constant 75 psia pressure. Temperature was maintained at 160° C. A total of 200 grams of ethylene oxide was charged to the reactor. The reactor was maintained for an additional 1 hour to consume unreacted ethylene oxide in the system. Catalyst activity was measured according to the amount of time in took to consume 200 grams of ethylene oxide at the constant EO gas pressures.

The results are shown in the following Table:
Results of Catalyst Activity for the Ethoxylation of NEODOL 23

| Metal Source | Catalyst Type | wt. Cat. (g) EO | Time of EO addition (min) |
| --- | --- | --- | --- |
| Nitrate Salt | LAPO 1 | 0.5 | 85 |
| Carbonate | REPO 1 | 0.5 | 34 |
| Carbonate | REPO 2 | 0.5 | 27 |
| Carbonate | REPO 3 | 0.5 | 33 |
| Carbonate | LAPO 2 | 0.5 | 29 |
| Carbonate | LAPO 3 | 0.5 | 36 |
| Carbonate | REPO 4 | 0.5 | 30 |

The carbonate derived LAPO and REPO catalysts consistently demonstrated at least 1.5 times the catalytic activity of the nitrate derived LAPO's, typically from about 2 to about 4 times the catalytic activity of the nitrate derived LAPO's.

EXAMPLE 3

LAPO catalysts were prepared varying certain parameters. The catalytic activity of the resulting catalysts was then evaluated to determine the impact of those parameters on catalytic activity.

A. Standard LAPO Catalyst (LAPO 1A)

A slurry of lanthanum carbonate hydrate in distilled $H_2O$ was prepared by addition of 31.2 g (0.068 moles) of carbonate to 200 ml of $N_2$ degassed distilled $H_2O$. A phosphoric acid solution was prepared by dissolving 16.5 g of 85% $H_3PO_4$ (0.143 moles) in 200 ml of $N_2$ degassed distilled $H_2O$. The acid solution was placed in a 1000 ml glass reactor equipped with reflux condenser, $N_2$ inlet, overhead stirrer and thermowell. The carbonate slurry was added to the acid solution at 25° C. over 15 minutes. The reaction was heated to 100° C. for 3 hours. The reaction mixture was cooled and the product filtered. The white solids were transferred to the reaction vessel and treated with 500 ml of $N_2$ degassed distilled $H_2O$ at 50° C. for 30 minutes with rapid stirring. The product was cooled and the solids filtered. The white solids were transferred to the reaction vessel and treated with a solution of 10 ml of 10N $NH_4OH$ dissolved in 500 ml of distilled $H_2O$. The mixture was stirred rapidly at 50° C. for 30 minutes. The reaction mixture was cooled to 25° C., and the product was isolated by vacuum filtration. The white solids were dried overnight at 50° C. using full vacuum. The white filter cake was ground using a mortar and pestle producing 29.2 grams of product.

B. Reverse Addition (LAPO 1B)

A catalyst was prepared according to the procedures described in paragraph A in all respects except that the phosphoric acid solution was added to the lanthanum carbonate slurry, the latter being contained in the reaction vessel.

C. Lower Temperature of Digestion Step (LAPO 1C)

A catalyst was prepared according to paragraph A in all respects except that the product was stirred at 25° C. instead of 100° C. for the 3 hour period.

D. Fast Addition of Carbonate Slurry to Acid (LAPO 1D)

A catalyst was prepared according to paragraph A in all respects except that the carbonate slurry was added in 15–20 seconds instead of 15 minutes.

E. High Temperature Addition of Slurry to Acid (LAPO 1E)

A catalyst was prepared according to paragraph A in all respects except that the carbonate slurry was added to the acid at 95° C. over 15 minutes.

F. Elimination of $NH_4OH$ Treatment (LAPO 1F)

A catalyst was prepared according to Example 1 in all respects except that the $NH_4OH$ treatment step was eliminated. Instead, after the first water wash, the catalyst was filtered and dried as described.

The foregoing catalysts were used to catalyze alkoxylation according to the general protocol outlined in paragraph A, with the following results:

| Catalyst type | Temp. of Add'n (° C.) | Time of Add'n (min) | Source/ Temperature of Digestion (° C.) | Method of Add'n/ $NH_4OH$ Treatment | Rate of EO Add'n (min) |
| --- | --- | --- | --- | --- | --- |
| Supplier | — | — | nitrate/— | —/— | 69 |
| LAPO 1A | 20 | 20 | carbonate/100 | slurry to acid/yes | 35 |
| LAPO 1B | 25 | 20 | carbonate/100 | acid to slurry/yes | 18 |
| LAPO 1C | 25 | 20 | carbonate/25 | slurry to acid/yes | 37 |
| LAPO 1D | 25 | 5 | carbonate/100 | slurry to acid/yes | 24 |
| LAPO 1E | 100 | 20 | carbonate/100 | slurry to acid/yes | 42 |
| LAPO 1F | 25 | 20 | carbonate/100 | slurry to acid/no | 24 |

The batch times for each carbonate derived LAPO was approximately 2–4 times faster than the nitrate derived material. Suprisingly, the addition of aqueous phosphoric acid to the carbonate slurry produced the most active catalyst. This is a positive finding as it is much easier to pump acid to a slurry system than the reverse. The lack of $NH_4OH$ treatment produced a very active catalyst; however, PEG and other side products tend to be higher when this neutralization step is eliminated.

EXAMPLE 4

While all lanthanide phosphates will act as ethoxylation catalysts, that activity generally decreases as the atomic weight increases. The following experiment evaluates various salts of cerium, praseodymium and neodymium, since these lanthanides show greater overall activity for ethoxylation than do the rest of the series. Thirteeen lanthanide salts were prepared using the same catalyst synthesis protocol and were evaluated each under the same ethoxylation protocol.

The order of catalyst synthesis was randomized, as was the order of ethoxylation experiments. The data in the following table is organized according to the lanthanide precursor used, and general order of activity. A standard lanthanum phosphate catalyst, prepared from lanthanum nitrate by a toll contractor, was used at the beginning, in the middle and at the end of the series to verify repeatability. This was done to ensure there was no bias in the data from a historical (order of evaluation) perspective.

A solution or slurry of the lanthanide salt was prepared in 200 ml of $N_2$ sparged DI water in a 1000 ml flask equipped with an overhead stirrer, 250 ml pressure equalized dropping funnel, reflux condenser, $N_2$ sparger and thermo well. For each experiment, 0.68 moles of the salt was used. For the first experiment, this amounted to 31.2 g of lanthanum carbonate (assumed m.w.=458). The amount of acid was adjusted depending upon whether the salt had the following formulas (i.e. whether there are two atoms of Ln per molecule or one atom of Ln per molecule):

| Lanthanide Salt Formula | Amount $H_3PO_4$ Used (20 m % excess) | Moles Lanthanide Salt |
|---|---|---|
| $Ln_2(X)_3$ | 0.143 | 0.068 |
| $LnY_3$ | 0.071 | 0.068 |

In the foregoing formulas, $X=CO_3$, $SO_4$ and $Y=Cl-$, $NO_3-$, acetate-.

A phosphoric acid solution was prepared by dissolving 16.5 g of 85% $H_3PO_4$ 0.143 moles) in 200 ml of $N_2$ sparged DI $H_2O$. The phosphoric acid solution was transferred to the addition funnel. If the salt had the formula $LnY_3$, only 8.25 g of 85% $H_3PO_4$ (0.071 moles) in 200 ml of $N_2$ sparged DI $H_2O$ was used. The phosphoric acid solution was added to the well stirred lanthanide salt/$H_2O$ mixture in equal portions over 15 minutes at 25° C. The reaction mixture was heated to reflux (100° C.) for 3 hours. The product was cooled and filtered. The product was then taken up into 500 ml of $H_2O$, added to reactor, and mixed well for 30 minutes at 50° C., after which the product was cooled and filtered product. The product was then taken up into 500 ml of $H_2O$ and added to the reactor. 10 ml of 1ON $NH_4OH$ was added and mixed well for 30 minutes at 50° C. The resulting product was cooled, the pH measured, and the product filtered. The product was air dried by letting air flow through filtered powder overnight. Thereafter, the product was dried further at 50° C. at full vacuum in a vacuum oven. The resulting catalyst was weighed and sent in for thermographic analysis (TGA).

The lanthanide salts were tested in the following order:
1. Lanthanum Carbonate (as a standard)
2. Cerium acetate
3. Praseodymium chloride
4. Neodymium carbonate
5. Neodymium chloride
6. Cerium chloride,
7. Lanthanum chloride
8. Lanthanum sulfate
9. Praseodymium acetate
10. Praseodymium carbonate
11. Cerium carbonate
12. Neodymium acetate
13. Lanthanum acetate The ethoxylation protocol was the same as in Example 2.
The results are given in the following Table:
Activity of Various Lanthanide Phosphate Catalysts for Ethoxylation of NEODOL 23 Alcohol

| Precursor Salt | Product | Activity (min) |
|---|---|---|
| lanthanum nitrate | lanthanum phosphate | 88 |
| lanthanum carbonate | lanthanum phosphate | 26 |
| lanthanum sulfate | lanthanum phosphate | 121 |
| lanthanum acetate | lanthanum phosphate | 45 |
| lanthanum chloride | lanthanum phosphate | 32 |
| praseodymium carbonate | praseodymium phosphate | 29 |
| praseodymium chloride | praseodymium phosphate | 45 |
| praseodymium acetate | praseodymium phosphate | 46 |
| lanthanum nitrate | lanthanum phosphate | 75 |
| neodymium carbonate | neodymium phosphate | 23 |
| neodymium chloride | neodymium phosphate | 49 |
| neodymium acetate | neodymium phosphate | 45 |
| cerium carbonate | cerium phosphate | 39 |
| cerium chloride | cerium phosphate | 50 |
| cerium acetate | cerium phosphate | 39 |
| lanthanum nitrate | lanthanum phosphate | 90 |

One lanthanide salt (cerium acetate) produced a catalyst with similar activity as the comparable carbonate precursor. However, none of the lanthanide salts produced a more active lanthanide phosphate than lanthanide carbonate.

Persons of ordinary skill in the art will recognize that many modifications may be made to the foregoing without departing from the spirit and scope thereof. The embodiment described herein is meant to be illustrative only and should not be taken as limiting the invention, which is defined in the following claims.

We claim:

1. A method for ensuring production of efficient rare earth metal phosphate catalysts for alkoxylation of organic compounds, said method comprising:
   selecting as a reactant one or more carbonate salts of said one or more rare earth metals;
   reacting said one or more carbonate salts with a source of phosphate under conditions effective to produce said efficient rare earth metal phosphate catalysts;
   wherein said efficient rare earth metal phosphate catalysts comprise increased activity for said alkoxylation compared to activity of substantially the same catalyst produced when one or more salts other than carbonate salts of said rare earth metals are selected as said reactant.

2. The method of claim 1 wherein said increased activity for said alkoxylation is at least 1.5 times activity of substantially the same rare earth metal phosphate catalyst produced when one or more salts other than carbonate salts of said one or more rare earth metals are selected as said reactant.

3. The method of claim 2 wherein said efficient rare earth metal comprises a metal selected from the group consisting of those having atomic numbers 39 and 57 through 71.

4. The method of claim 2 wherein said efficient rare earth metal phosphate catalyst comprises a catalytically effective amount of one or more phosphate salts of elements selected from the group consisting of cerium, lanthanum, praseodymium, neodymium, yttrium, samarium, gadolinium, dysprosium, erbium, and ytterbium.

5. The method of claim 2 comprising obtaining said metal from natural mineral ore.

6. The method of claim 2 wherein said efficient rare earth metal phosphate catalyst comprises one or more rare earth elements selected from the group consisting of bastnasite, monazite, xenotime, didymium, gadolinite and euxenite.

7. The method of claim 6 comprising obtaining said metal from natural mineral ore.

8. The method of claim 1 wherein said increased activity for said alkoxylation is at least 2 times activity of substantially the same rare earth metal phosphate catalyst produced when one or more salts other than carbonate salts of said one or more rare earth metals are selected as said reactant.

9. The method of claim 8 wherein said efficient rare earth metal comprises a metal selected from the group consisting of those having atomic numbers 39 and 57 through 71.

10. The method of claim 8 wherein said efficient rare earth metal phosphate catalyst comprises a catalytically effective amount of one or more phosphate salts of elements selected from the group consisting of cerium, lanthanum, praseodymium, neodymium, yttrium, samarium, gadolinium, dysprosium, erbium, and ytterbium.

11. The method of claim 1 wherein said increased activity for said alkoxylation is at least 3 times activity of substantially the same rare earth metal phosphate catalyst produced when one or more salts other than carbonate salts of said one or more rare earth metals are selected as said reactant.

12. The method of claim 1 wherein said efficient rare earth metal comprises a metal selected from the group consisting of those having atomic numbers 39 and 57 through 71.

13. The method of claim 1 wherein said efficient catalyst comprises a catalytically effective amount of one or more phosphate salts of elements selected from the group consisting of cerium, lanthanum, praseodymium, neodymium, yttrium, samarium, gadolinium, dysprosium, erbium, and ytterbium.

14. The method of claim 1 wherein said conditions comprise mixing said one or more carbonate salts of said one or more rare earth metals with a volume of water to form a carbonate slurry.

15. The method of claim 14 wherein said one or more carbonate salts comprise from about 8% to about 15% Ce, from about 44% to about 65% La, from about 20% to about 25% Nd, and from about 2% to about 10% Pr.

16. The method of claim 15 wherein said conditions comprise preparing an aqueous solution of from about 5% to about 15% phosphoric acid with agitation at a temperature of from about 25° C. to about 80° C.

17. The method of claim 16 wherein said conditions further comprise adding said carbonate slurry to said aqueous solution of phosphoric acid under slurrying conditions effective to produce a reaction mixture.

18. The method of claim 17 wherein said slurrying conditions comprise agitation at a temperature of from about 25° C. to about 100° C. over a slurrying period of time sufficient to consume said carbonate.

19. The method of claim 18 wherein said slurrying period of time is from about 10 minutes to about 60 minutes.

20. The method of claim 19 further comprising
cooling said reaction mixture to a slurrying temperature effective to produce first solids; and
subjecting said first solids to second slurrying conditions effective to separate said first solids from said reaction mixture and to form an aqueous second slurry comprising said first solids.

21. The method of claim 20 wherein said second slurrying conditions comprise stirring at a temperature of from about 25° C. to about 80° C. for from about 10 minutes to about 60 minutes to produce a heated second slurry.

22. The method of claim 21 further comprising
cooling said heated second slurry, preferably to about 25° C., producing a cooled second slurry comprising second solids; and
subjecting said second solids to neutralizing conditions effective to neutralize said mixture, producing a neutralized second slurry comprising neutralized solids.

23. The method of claim 22 wherein said neutralizing conditions comprise adding aqueous $NH_4OH$.

24. The method of claim 23 further comprising
cooling said neutralized second slurry to a temperature effective to produce said neutralized solids; and,
collecting said neutralized solids.

25. The method of claim 24 further comprising drying said neutralized solids to produce a cake comprising said one or more phosphate salts of said one or more rare earth elements.

26. The method of claim 25 further comprising grinding said cake to produce a free flowing powder.

27. The method of claim 16 wherein said conditions further comprise adding said aqueous phosphoric acid to said carbonate slurry under slurrying conditions effective to produce a reaction mixture.

28. The method of claim 27 wherein said slurrying conditions comprise agitation at a temperature of from about 25° C. to about 100° C. over a slurrying period of time sufficient to consume said carbonate.

29. The method of claim 28 wherein said slurrying period of time is from about 10 minutes to about 60 minutes.

30. The method of claim 29 further comprising
cooling said reaction mixture to a slurrying temperature effective to produce first solids; and
subjecting said first solids to second slurrying conditions effective to separate said first solids from said reaction mixture and to form an aqueous second slurry comprising said first solids.

31. The method of claim 30 wherein said second slurrying conditions comprise stirring at a temperature of from about 25° C. to about 80° C. for from about 10 minutes to about 60 minutes to produce a heated second slurry.

32. The method of claim 31 further comprising
cooling said heated second slurry, preferably to about 25° C., producing a cooled second slurry comprising second solids; and
subjecting said second solids to neutralizing conditions effective to neutralize said mixture, producing a neutralized second slurry comprising neutralized solids.

33. The method of claim 32 wherein said neutralizing conditions comprise adding aqueous $NH_4OH$.

34. The method of claim 33 further comprising
cooling said neutralized second slurry to a temperature effective to produce said neutralized solids; and,
collecting said neutralized solids.

35. The method of claim 34 further comprising drying said neutralized solids to produce a cake comprising said one or more phosphate salts of said one or more rare earth elements.

36. The method of claim 35 further comprising grinding said cake to produce a free flowing powder.

37. The method of claim 14 wherein said one or more carbonate salts are carbonates of the following metals in the following quantities: 12.5% w Ce, 59.3% w La, 22.4% w Nd and 5.8% Pr.

38. The method of claim 37 wherein said conditions comprise preparing an aqueous solution of from about 5% to about 15% phosphoric acid with agitation at a temperature of from about 25° C. to about 80° C.

39. The method of claim 38 wherein said conditions further comprise adding said carbonate slurry to said aqueous solution of phosphoric acid under slurrying conditions effective to produce a reaction mixture.

40. The method of claim 38 wherein said conditions further comprise adding said aqueous phosphoric acid to said carbonate slurry under slurrying conditions effective to produce a reaction mixture.

41. The method of claim 40 wherein said slurrying conditions comprise agitation at a temperature of from about 25° C. to about 100° C. over a slurrying period of time sufficient to consume said carbonate.

42. The method of claim 41 wherein said slurrying period of time is from about 10 minutes to about 60 minutes.

43. The method of claim 42 further comprising
cooling said reaction mixture to a slurrying temperature effective to produce first solids; and
subjecting said first solids to second slurrying conditions effective to separate said first solids from said reaction mixture and to form an aqueous second slurry comprising said first solids.

44. The method of claim 43 wherein said second slurrying conditions comprise stirring at a temperature of from about 25° C. to about 80° C. for from about 10 minutes to about 60 minutes to produce a heated second slurry.

45. The method of claim 44 further comprising
cooling said heated second slurry, preferably to about 25° C., producing a cooled second slurry comprising second solids; and
subjecting said second solids to neutralizing conditions effective to neutralize said mixture, producing a neutralized second slurry comprising neutralized solids.

46. The method of claim 45 wherein said neutralizing conditions comprise adding aqueous NH$_4$OH.

47. The method of claim 46 further comprising
cooling said neutralized second slurry to a temperature effective to produce said neutralized solids; and,
collecting said neutralized solids.

48. The method of claim 47 further comprising drying said neutralized solids to produce a cake comprising said one or more phosphate salts of said one or more rare earth elements.

49. The method of claim 48 further comprising grinding said cake to produce a free flowing powder.

50. The method of claim 39 wherein said slurrying conditions comprise agitation at a temperature of from about 25° C. to about 100° C. over a slurrying period of time sufficient to consume said carbonate.

51. The method of claim 50 wherein said slurrying period of time is from about 10 minutes to about 60 minutes.

52. The method of claim 51 further comprising
cooling said reaction mixture to a slurrying temperature effective to produce first solids; and
subjecting said first solids to second slurrying conditions effective to separate said first solids from said reaction mixture and to form an aqueous second slurry comprising said first solids.

53. The method of claim 52 wherein said second slurrying conditions comprise stirring at a temperature of from about 25° C. to about 80° C. for from about 10 minutes to about 60 minutes to produce a heated second slurry.

54. The method of claim 53 further comprising
cooling said heated second slurry, preferably to about 25° C., producing a cooled second slurry comprising second solids; and
subjecting said second solids to neutralizing conditions effective to neutralize said mixture, producing a neutralized second slurry comprising neutralized solids.

55. The method of claim 54 wherein said neutralizing conditions comprise adding aqueous NH$_4$OH.

56. The method of claim 55 further comprising
cooling said neutralized second slurry to a temperature effective to produce said neutralized solids; and,
collecting said neutralized solids.

57. The method of claim 56 further comprising drying said neutralized solids to produce a cake comprising said one or more phosphate salts of said one or more rare earth elements.

58. The method of claim 57 further comprising grinding said cake to produce a free flowing powder.

59. The method of claim 14 wherein said conditions comprise preparing an aqueous solution of from about 5% to about 15% phosphoric acid with agitation at a temperature of from about 25° C. to about 80° C.

60. The method of claim 59 wherein said conditions further comprise adding said carbonate slurry to said aqueous solution of phosphoric acid under slurrying conditions effective to produce a reaction mixture.

61. The method of claim 60 wherein said slurrying conditions comprise agitation at a temperature of from about 25° C. to about 100° C. over a slurrying period of time sufficient to consume said carbonate.

62. The method of claim 61 wherein said slurrying period of time is from about 10 minutes to about 60 minutes.

63. The method of claim 62 further comprising
cooling said reaction mixture to a slurrying temperature effective to produce first solids; and
subjecting said first solids to second slurrying conditions effective to separate said first solids from said reaction mixture and to form an aqueous second slurry comprising said first solids.

64. The method of claim 63 wherein said second slurrying conditions comprise stirring at a temperature of from about 25° C. to about 80° C. for from about 10 minutes to about 60 minutes to produce a heated second slurry.

65. The method of claim 64 further comprising
cooling said heated second slurry, preferably to about 25° C., producing a cooled second slurry comprising second solids; and
subjecting said second solids to neutralizing conditions effective to neutralize said mixture, producing a neutralized second slurry comprising neutralized solids.

66. The method of claim 65 wherein said neutralizing conditions comprise adding aqueous NH$_4$OH.

67. The method of claim 65 further comprising
cooling said neutralized second slurry to a temperature effective to produce said neutralized solids; and,
collecting said neutralized solids.

68. The method of claim 67 further comprising drying said neutralized solids to produce a cake comprising said one or more phosphate salts of said one or more rare earth elements.

69. The method of claim 68 further comprising grinding said cake to produce a free flowing powder.

70. The method of claim 65 further comprising
cooling said neutralized second slurry to a temperature effective to produce said neutralized solids; and,
collecting said neutralized solids.

71. The method of claim 70 further comprising drying said neutralized solids to produce a cake comprising said one or more phosphate salts of said one or more rare earth elements.

72. The method of claim 71 further comprising grinding said cake to produce a free flowing powder.

73. The method of claim 72 further comprising grinding said cake to produce a free flowing powder.

74. The method of claim 59 wherein said conditions further comprise adding said aqueous phosphoric acid to said carbonate slurry under slurrying conditions effective to produce a reaction mixture.

75. The method of claim 74 wherein said slurrying conditions comprise agitation at a temperature of from about 25° C. to about 100° C. over a slurrying period of time sufficient to consume said carbonate.

76. The method of claim 75 wherein said slurrying period of time is from about 10 minutes to about 60 minutes.

77. The method of claim 76 further comprising cooling said reaction mixture to a slurrying temperature effective to produce first solids; and subjecting said first solids to second slurrying conditions effective to separate said first solids from said reaction mixture and to form an aqueous second slurry comprising said first solids.

78. The method of claim 77 wherein said second slurrying conditions comprise stirring at a temperature of from about 25° C. to about 80° C. for from about 10 minutes to about 60 minutes to produce a heated second slurry.

79. The method of claim 78 further comprising cooling said heated second slurry, preferably to about 25° C., producing a cooled second slurry comprising second solids; and subjecting said second solids to neutralizing conditions effective to neutralize said mixture, producing a neutralized second slurry comprising neutralized solids.

80. The method of claim 79 wherein said neutralizing conditions comprise adding aqueous $NH_4OH$.

81. The method of claim 80 further comprising cooling said neutralized second slurry to a temperature effective to produce said neutralized solids; and, collecting said neutralized solids.

82. The method of claim 81 further comprising drying said neutralized solids to produce a cake comprising said one or more phosphate salts of said one or more rare earth elements.

83. The method of claim 82 further comprising grinding said cake to produce a free flowing powder.

84. A method for ensuring production of efficient rare earth metal phosphate catalysts for alkoxylation of organic compounds, said method comprising:

selecting as a reactant one or more carbonate salts of one or more lanthanum series metals;

reacting said one or more carbonate salts with a source of phosphate under conditions effective to produce efficient lanthanum phosphate catalysts;

wherein said efficient lanthanum phosphate catalysts comprise increased activity for said alkoxylation compared to activity of substantially the same lanthanum phosphate catalyst produced when one or more salts other than carbonate salts of said lanthanum series metal are selected as said reactant.

85. The method of claim 84 wherein said increased activity for said alkoxylation is at least 1.5 times activity of substantially the same lanthanum phosphate catalyst produced when one or more salts other than carbonate salts of said one or more lanthanum series metal are selected as said reactant.

86. The method of claim 85 comprising obtaining said one or more lanthanum series metal from natural mineral ore.

87. The method of claim 85 wherein said conditions comprise mixing said one or more carbonate salts of said one or more lanthanum series metals with a volume of water to form a carbonate slurry.

88. The method of claim 87 wherein said conditions comprise preparing an aqueous solution of from about 5% to about 15% phosphoric acid with agitation at a temperature of from about 25° C. to about 80° C.

89. The method of claim 88 wherein said conditions further comprise adding said carbonate slurry to said aqueous solution of phosphoric acid under slurrying conditions effective to produce a reaction mixture.

90. The method of claim 89 wherein said slurrying conditions comprise agitation at a temperature of from about 25° C. to about 100° C. over a slurrying period of time sufficient to consume said carbonate.

91. The method of claim 90 wherein said slurrying period of time is from about 10 minutes to about 60 minutes.

92. The method of claim 91 further comprising cooling said reaction mixture to a slurrying temperature effective to produce first solids; and subjecting said first solids to second slurrying conditions effective to separate said first solids from said reaction mixture and to form an aqueous second slurry comprising said first solids.

93. The method of claim 92 wherein said second slurrying conditions comprise stirring at a temperature of from about 25° C. to about 80° C. for from about 10 minutes to about 60 minutes to produce a heated second slurry.

94. The method of claim 93 further comprising cooling said heated second slurry, preferably to about 25° C., producing a cooled second slurry comprising second solids; and subjecting said second solids to neutralizing conditions effective to neutralize said mixture, producing a neutralized second slurry comprising neutralized solids.

95. The method of claim 94 wherein said neutralizing conditions comprise adding aqueous $NH_4OH$.

96. The method of claim 95 further comprising cooling said neutralized second slurry to a temperature effective to produce said neutralized solids; and, collecting said neutralized solids.

97. The method of claim 96 further comprising drying said neutralized solids to produce a cake comprising said one or more phosphate salts of said one or more rare earth elements.

98. The method of claim 97 further comprising grinding said cake to produce a free flowing powder.

99. The method of claim 88 wherein said conditions further comprise adding said aqueous phosphoric acid to said carbonate slurry under slurrying conditions effective to produce a reaction mixture.

100. The method of claim 99 wherein said slurrying conditions comprise agitation at a temperature of from about 25° C. to about 100° C. over a slurrying period of time sufficient to consume said carbonate.

101. The method of claim 100 wherein said slurrying period of time is from about 10 minutes to about 60 minutes.

102. The method of claim 101 further comprising cooling said reaction mixture to a slurrying temperature effective to produce first solids; and subjecting said first solids to second slurrying conditions effective to separate said first solids from said reaction mixture and to form an aqueous second slurry comprising said first solids.

103. The method of claim 102 wherein said second slurrying conditions comprise stirring at a temperature of from about 25° C. to about 80° C. for from about 10 minutes to about 60 minutes to produce a heated second slurry.

104. The method of claim 103 further comprising
  cooling said heated second slurry, preferably to about 25° C., producing a cooled second slurry comprising second solids; and
  subjecting said second solids to neutralizing conditions effective to neutralize said mixture, producing a neutralized second slurry comprising neutralized solids.

105. The method of claim 104 wherein said neutralizing conditions comprise adding aqueous $NH_4OH$.

106. The method of claim 105 further comprising
  cooling said neutralized second slurry to a temperature effective to produce said neutralized solids; and,
  collecting said neutralized solids.

107. The method of claim 106 further comprising drying said neutralized solids to produce a cake comprising said one or more phosphate salts of said one or more rare earth elements.

108. The method of claim 107 further comprising grinding said cake to produce a free flowing powder.

109. The method of claim 104 further comprising
  cooling said neutralized second slurry to a temperature effective to produce said neutralized solids; and,
  collecting said neutralized solids.

110. The method of claim 109 further comprising drying said neutralized solids to produce a cake comprising said one or more phosphate salts of said one or more rare earth elements.

111. The method of claim 110 further comprising grinding said cake to produce a free flowing powder.

112. The method of claim 84 wherein said increased activity for said alkoxylation is at least 2 times activity of substantially the same lanthanum phosphate catalyst produced when one or more salts other than carbonate salts of said one or more lanthanum series metal is selected as said reactant.

113. The method of claim 84 wherein said increased activity for said alkoxylation is at least 3 times activity of substantially the same lanthanum phosphate catalyst produced when one or more salts other than carbonate salts of said one or more lanthanum series metal are selected as said reactant.

114. The method of claim 84 comprising obtaining said one or more lanthanum series metals from natural mineral ore.

115. The method of claim 84 wherein said conditions comprise mixing said one or more carbonate salts of said one or more lanthanum series metals with a volume of water to form a carbonate slurry.

116. The method of claim 115 wherein said conditions comprise preparing an aqueous solution of from about 5% to about 15% phosphoric acid with agitation at a temperature of from about 25° C. to about 80° C.

117. The method of claim 116 wherein said conditions further comprise adding said carbonate slurry to said aqueous solution of phosphoric acid under slurrying conditions effective to produce a reaction mixture.

118. The method of claim 117 wherein said slurrying conditions comprise agitation at a temperature of from about 25° C. to about 100° C. over a slurrying period of time sufficient to consume said carbonate.

119. The method of claim 118 wherein said slurrying period of time is from about 10 minutes to about 60 minutes.

120. The method of claim 119 further comprising
  cooling said reaction mixture to a slurrying temperature effective to produce first solids; and
  subjecting said first solids to second slurrying conditions effective to separate said first solids from said reaction mixture and to form an aqueous second slurry comprising said first solids.

121. The method of claim 120 wherein said second slurrying conditions comprise stirring at a temperature of from about 25° C. to about 80° C. for from about 10 minutes to about 60 minutes to produce a heated second slurry.

122. The method of claim 121 further comprising
  cooling said heated second slurry, preferably to about 25° C., producing a cooled second slurry comprising second solids; and
  subjecting said second solids to neutralizing conditions effective to neutralize said mixture, producing a neutralized second slurry comprising neutralized solids.

123. The method of claim 122 wherein said neutralizing conditions comprise adding aqueous $NH_4OH$.

124. The method of claim 123 further comprising
  cooling said neutralized second slurry to a temperature effective to produce said neutralized solids; and,
  collecting said neutralized solids.

125. The method of claim 124 further comprising drying said neutralized solids to produce a cake comprising said one or more phosphate salts of said one or more rare earth elements.

126. The method of claim 125 further comprising grinding said cake to produce a free flowing powder.

127. The method of claim 116 wherein said conditions further comprise adding said aqueous phosphoric acid to said carbonate slurry under slurrying conditions effective to produce a reaction mixture.

128. The method of claim 127 wherein said slurring conditions comprise agitation at a temperature of from about 25° C. to about 100° C. over a slurrying period of time sufficient to consume said carbonate.

129. The method of claim 128 wherein said slurrying period of time is from about 10 minutes to about 60 minutes.

130. The method of claim 129 further comprising
  cooling said reaction mixture to a slurrying temperature effective to produce first solids; and
  subjecting said first solids to second slurrying conditions effective to separate said first solids from said reaction mixture and to form an aqueous second slurry comprising said first solids.

131. The method of claim 130 wherein said second slurrying conditions comprise stirring at a temperature of from about 25° C. to about 80° C. for from about 10 minutes to about 60 minutes to produce a heated second slurry.

132. The method of claim 131 further comprising
  cooling said heated second slurry, preferably to about 25° C., producing a cooled second slurry comprising second solids; and
  subjecting said second solids to neutralizing conditions effective to neutralize said mixture, producing a neutralized second slurry comprising neutralized solids.

133. The method of claim 132 wherein said neutralizing conditions comprise adding aqueous $NH_4OH$.

134. The method of claim 133 further comprising
  cooling said neutralized second slurry to a temperature effective to produce said neutralized solids; and,
  collecting said neutralized solids.

135. The method of claim 134 further comprising drying said neutralized solids to produce a cake comprising said one or more phosphate salts of said one or more rare earth elements.

136. The method of claim 135 further comprising grinding said cake to produce a free flowing powder.

137. A method for ensuring production of efficient rare earth metal phosphate catalysts for alkoxylation of organic compounds, said method comprising:
  selecting as a reactant one or more carbonate salts of lanthanum elements (atomic numbers 57–71);
  reacting said one or more carbonate salts with a source of phosphate under conditions effective to produce efficient lanthanum phosphate catalysts (LAPO's);
  wherein said efficient lanthanum phosphate catalysts comprise increased activity for said alkoxylation compared to activity of substantially the same lanthanum phosphate catalyst produced when one or more salts other than carbonate salts of said lanthanum are selected as said reactant.

138. The method of claim 137 wherein said increased activity for said alkoxylation is at least 1.5 times activity of substantially the same rare earth metal phosphate catalyst produced when one or more salts other than carbonate salts of said one or more rare earth metals are selected as said reactant.

139. The method of claim 138 comprising obtaining said metal from natural mineral ore.

140. The method of claim 138 wherein said conditions comprise mixing said one or more carbonate salts of said one or more rare earth metals with a volume of water to form a carbonate slurry.

141. The method of claim 140 wherein said conditions comprise preparing an aqueous solution of from about 5% to about 15% phosphoric acid with agitation at a temperature of from about 25° C. to about 80° C.

142. The method of claim 141 wherein said conditions further comprise adding said carbonate slurry to said aqueous solution of phosphoric acid under slurrying conditions effective to produce a reaction mixture.

143. The method of claim 141 wherein said conditions further comprise adding said aqueous phosphoric acid to said carbonate slurry under slurrying conditions effective to produce a reaction mixture.

144. The method of claim 143 wherein said slurrying conditions comprise agitation at a temperature of from about 25° C. to about 100° C. over a slurrying period of time sufficient to consume said carbonate.

145. The method of claim 144 wherein said slurrying period of time is from about 10 minutes to about 60 minutes.

146. The method of claim 145 further comprising
  cooling said reaction mixture to a slurrying temperature effective to produce first solids; and
  subjecting said first solids to second slurrying conditions effective to separate said first solids from said reaction mixture and to form an aqueous second slurry comprising said first solids.

147. The method of claim 146 wherein said second slurrying conditions comprise stirring at a temperature of from about 25° C. to about 80° C. for from about 10 minutes to about 60 minutes to produce a heated second slurry.

148. The method of claim 147 further comprising
  cooling said heated second slurry, preferably to about 25° C., producing a cooled second slurry comprising second solids; and
  subjecting said second solids to neutralizing conditions effective to neutralize said mixture, producing a neutralized second slurry comprising neutralized solids.

149. The method of claim 148 wherein said neutralizing conditions comprise adding aqueous $NH_4OH$.

150. The method of claim 149 further comprising
  cooling said neutralized second slurry to a temperature effective to produce said neutralized solids; and,
  collecting said neutralized solids.

151. The method of claim 150 further comprising drying said neutralized solids to produce a cake comprising said one or more phosphate salts of said one or more rare earth elements.

152. The method of claim 151 further comprising grinding said cake to produce a free flowing powder.

153. The method of claim 142 wherein said slurrying conditions comprise agitation at a temperature of from about 25° C. to about 100° C. over a slurrying period of time sufficient to consume said carbonate.

154. The method of claim 153 wherein said slurrying period of time is from about 10 minutes to about 60 minutes.

155. The method of claim 154 further comprising
  cooling said reaction mixture to a slurrying temperature effective to produce first solids; and
  subjecting said first solids to second slurrying conditions effective to separate said first solids from said reaction mixture and to form an aqueous second slurry comprising said first solids.

156. The method of claim 155 wherein said second slurrying conditions comprise stirring at a temperature of from about 25° C. to about 80° C. for from about 10 minutes to about 60 minutes to produce a heated second slurry.

157. The method of claim 156 further comprising
  cooling said heated second slurry, preferably to about 25° C., producing a cooled second slurry comprising second solids; and
  subjecting said second solids to neutralizing conditions effective to neutralize said mixture, producing a neutralized second slurry comprising neutralized solids.

158. The method of claim 157 wherein said neutralizing conditions comprise adding aqueous $NH_4OH$.

159. The method of claim 153 further comprising
  cooling said neutralized second slurry to a temperature effective to produce said neutralized solids; and,
  collecting said neutralized solids.

160. The method of claim 159 further comprising drying said neutralized solids to produce a cake comprising said one or more phosphate salts of said one or more rare earth elements.

161. The method of claim 160 further comprising grinding said cake to produce a free flowing powder.

162. The method of claim 137 wherein said increased activity for said alkoxylation is at least 2 times activity of substantially the same rare earth metal phosphate catalyst produced when one or more salts other than carbonate salts of said one or more rare earth metals are selected as said reactant.

163. The method of claim 137 wherein said increased activity for said alkoxylation is at least 3 times activity of substantially the same rare earth metal phosphate catalyst produced when one or more salts other than carbonate salts of said one or more rare earth metals are selected as said reactant.

164. The method of claim 137 comprising obtaining said metal from natural mineral ore.

165. The method of claim 137 wherein said conditions comprise mixing said one or more carbonate salts of said one or more rare earth metals with a volume of water to form a carbonate slurry.

166. The method of claim 165 wherein said conditions comprise preparing an aqueous solution of from about 5% to about 15% phosphoric acid with agitation at a temperature of from about 25° C. to about 80° C.

167. The method of claim 166 wherein said conditions further comprise adding said carbonate slurry to said aqueous solution of phosphoric acid under slurrying conditions effective to produce a reaction mixture.

168. The method of claim 167 wherein said slurring period of time is from about 10 minutes to about 60 minutes.

169. The method of claim 167 wherein said slurrying conditions comprise agitation at a temperature of from about 25° C. to about 100° C. over a slurrying period of time sufficient to consume said carbonate.

170. The method of claim 168 further comprising
cooling said reaction mixture to a slurrying temperature effective to produce first solids; and
subjecting said first solids to second slurrying conditions effective to separate said first solids from said reaction mixture and to form an aqueous second slurry comprising said first solids.

171. The method of claim 170 wherein said second slurrying conditions comprise stirring at a temperature of from about 25° C. to about 80° C. for from about 10 minutes to about 60 minutes to produce a heated second slurry.

172. The method of claim 171 further comprising
cooling said heated second slurry, preferably to about 25° C., producing a cooled second slurry comprising second solids; and
subjecting said second solids to neutralizing conditions effective to neutralize said mixture, producing a neutralized second slurry comprising neutralized solids.

173. The method of claim 172 wherein said neutralizing conditions comprise adding aqueous $NH_4OH$.

174. The method of claim 173 further comprising
cooling said neutralized second slurry to a temperature effective to produce said neutralized solids; and,
collecting said neutralized solids.

175. The method of claim 174 further comprising drying said neutralized solids to produce a cake comprising said one or more phosphate salts of said one or more rare earth elements.

176. The method of claim 175 further comprising grinding said cake to produce a free flowing powder.

177. The method of claim 176 wherein said one or more lanthanum series metals comprise lanthanide metals (atomic numbers 58 through 71).

178. The method of claim 176 wherein said one or more lanthanum series metals comprise cerium earth group metals (atomic numbers 57 through 62).

179. The method of claim 176 wherein said one or more lanthanum series metals comprise terbium earth group metals (atomic numbers 63 through 66).

180. The method of claim 176 wherein said one or more lanthanum series metals comprise yttrium earth group metals (atomic numbers 67 through 71).

181. The method of claim 172 further comprising
cooling said neutralized second slurry to a temperature effective to produce said neutralized solids; and,
collecting said neutralized solids.

182. The method of claim 181 further comprising drying said neutralized solids to produce a cake comprising said one or more phosphate salts of said one or more rare earth elements.

183. The method of claim 182 further comprising grinding said cake to produce a free flowing powder.

184. The method of claim 166 wherein said conditions further comprise adding said aqueous phosphoric acid to said carbonate slurry under slurrying conditions effective to produce a reaction mixture.

185. The method of claim 184 wherein said slurrying conditions comprise agitation at a temperature of from about 25° C. to about 100° C. over a slurrying period of time sufficient to consume said carbonate.

186. The method of claim 185 wherein said slurrying period of time is from about 10 minutes to about 60 minutes.

187. The method of claim 186 further comprising
cooling said reaction mixture to a slurrying temperature effective to produce first solids; and
subjecting said first solids to second slurrying conditions effective to separate said first solids from said reaction mixture and to form an aqueous second slurry comprising said first solids.

188. The method of claim 187 wherein said second slurrying conditions comprise stirring at a temperature of from about 25° C. to about 80° C. for from about 10 minutes to about 60 minutes to produce a heated second slurry.

189. The method of claim 188 further comprising
cooling said heated second slurry, preferably to about 25° C., producing a cooled second slurry comprising second solids; and
subjecting said second solids to neutralizing conditions effective to neutralize said mixture, producing a neutralized second slurry comprising neutralized solids.

190. The method of claim 189 wherein said neutralizing conditions comprise adding aqueous $NH_4OH$.

191. The method of claim 190 further comprising
cooling said neutralized second slurry to a temperature effective to produce said neutralized solids; and,
collecting said neutralized solids.

192. The method of claim 191 further comprising drying said neutralized solids to produce a cake comprising said one or more phosphate salts of said one or more rare earth elements.

193. The method of claim 192 further comprises grinding said cake to produce a free flowing powder.

194. A method for ensuring production of efficient rare earth metal phosphate catalysts for alkoxylation of organic compounds, said method comprising:
selected as a reactant one or more carbonate salts of the rare earth metals selected from the group consisting of:
yttrium; or one of the lanthanide series elements (atomic numbers 58–71); or
one or more natural mineral ores selected from the group consisting of bastnasite, monazite, xenotime, didymium, gadolinite and euxenite; or
a mixture of rare earth metals comprising from about 8% to about 15% Ce, from about 44% to about 65% La, from about 20% to about 25% to about Nd, and from about 2% to about 10% Pr; or
a mixture of rare earth metals in the following quantities: 12.5% w Ce, 59.3% La, 22.4% w Nd and 5.8% w Pr; or
more than one of the rare earth metal elements selected from the group consisting of yttrium, lanthanum, cerium, praseodymium, neodymium, promethium, samarium, europium, gadolinium, dysprosium, holmium, erbium, thulium, ytterbium, and lutetium; or
more than one of the rare metal elements selected from the group consisting of yttrium, cerium, praseodymium, neodymium, promethium, samarium, europium, gadolinium, terbium, dysprosium, holmium, erbium, thulium, ytterbium, and lutetium; or
more than one of the rare earth metal elements selected from the group consisting of yttrium, lanthanum, praseodymium, neodymium, promethium, samarium, europium, gadolinium, tebium, dysprosium, holmium, erbium, thulium, ytterbium, and lutetium; and reacting said one or more carbonate salts with a source of phosphate under conditions effective to produce said efficient rare earth metal phosphate catalysts;

wherein said efficient rare earth metal phosphate catalysts comprise increased activity for said alkoxylation compared activity of substantially the same catalyst production when one or more salts other than carbonate salts of said rare earth metals are selected as said reactant.

195. The method of claim 194 comprising obtaining said metal from natural mineral ore.

196. The method of claim 194 wherein said conditions comprise mixing said one or more carbonate salts of said one or more rare earth metals with a volume of water to form a carbonate slurry.

197. The method of claim 196 wherein said conditions comprise preparing an aqueous solution of from about 5% to about 15% phosphoric acid with agitation at a temperature of from about 25° C. to about 80° C.

198. The method of claim 197 wherein said conditions further comprise combining said carbonate slurry with said aqueous solution of phosphoric acid under slurrying conditions effective to produce a reaction mixture.

199. The method of claim 198 wherein said slurrying conditions comprise agitation at a temperature of from about 25° C. to about 100° C. over a slurrying period of time sufficient to consume said carbonate.

200. The method of claim 199 wherein said slurrying period of time is from about 10 minutes to about 60 minutes.

201. The method of claim 200 further comprising cooling said reaction mixture to a slurrying temperature effective to produce first solids; and subjecting said first solids to second slurrying conditions effective to separate said first solids from said reaction mixture and to form an aqueous second slurry comprising said first solids.

202. The method of claim 201 wherein said second slurrying conditions comprise stirring at a temperature of from about 25° C. to about 80° C. for from about 10 minutes to about 60 minutes to produce a heated second slurry.

203. The method of claim 202 further comprising cooling said heated second slurry, preferably to about 25° C., producing a cooled second slurry comprising second solids; and subjecting said second solids to neutralizing conditions effective to neutralize said mixture, producing a neutralized second slurry comprising neutralized solids.

204. The method of claim 203 wherein said neutralizing conditions comprise adding aqueous $NH_4OH$.

205. The method of claim 204 further comprising cooling said neutralized second slurry to a temperature effective to produce said neutralized solids; and, collecting said neutralized solids.

206. The method of claim 205 further comprising drying said neutralized solids to produce a cake comprising said one or more phosphate salts of said one or more rare earth elements.

207. The method of claim 206 further comprising grinding said cake to produce a free flowing powder.

* * * * *